United States Patent
Tapalian et al.

(10) Patent No.: US 6,657,731 B2
(45) Date of Patent: Dec. 2, 2003

(54) COATED OPTICAL MICROCAVITY RESONATOR CHEMICAL SENSOR

(75) Inventors: Haig Charles Tapalian, Canton, MA (US); Juha-Pekka Laine, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 37 days.

(21) Appl. No.: 09/894,691

(22) Filed: Jun. 28, 2001

(65) Prior Publication Data

US 2002/0172457 A1 Nov. 21, 2002

Related U.S. Application Data

(60) Provisional application No. 60/214,383, filed on Jun. 28, 2000.

(51) Int. Cl.[7] .................................................. G01B 9/02
(52) U.S. Cl. ...................... 356/480; 356/481; 356/454; 356/517; 356/519
(58) Field of Search ................................. 356/450, 454, 356/477, 480, 481, 517, 519; 385/30, 28, 35, 12

(56) References Cited

U.S. PATENT DOCUMENTS

| | | |
|---|---|---|
| 4,695,121 A | 9/1987 | Mahapatra et al. |
| 4,807,232 A | 2/1989 | Hart et al. |
| 5,130,843 A | 7/1992 | He et al. |
| 5,268,693 A | 12/1993 | Walsh |
| 5,420,688 A | 5/1995 | Farah |
| 5,742,633 A | 4/1998 | Stone et al. |
| 6,009,115 A | 12/1999 | Ho |
| 6,023,540 A | 2/2000 | Walt et al. |
| 6,040,191 A | 3/2000 | Grow |
| 6,058,127 A | 5/2000 | Joannopoulos et al. |
| 6,266,459 B1 | 7/2001 | Walt et al. |
| 2002/0079453 A1 * | 6/2002 | Tapalian et al. ............ 250/343 |

OTHER PUBLICATIONS

Laine, J.P. et al., Silica microsphere resonator and SPARROW waveguide coupler structures, Integrated Photonics Research 2000, OSA Technical Digest, Quebec City, Canada, Jul. 2000.

Laine, J.P. et al., Microsphere resonator mode charaterization by pedestal anti–resonant reflecting waveguide coupler, IEEE Photonics Technology Letters, vol. 12, 1004–1006, 2000.

Little, B. et al., Pedestal antiresonant reflecting waveguides for robust coupling to microsphere resonators and for microphotonic circuits, Optics Letters, vol. 25, No. 1, pp. 73–75, 2000.

Laine, J.P. et al., Novel techniques for whispering–gallery––mode excitation in silica microspheres, Integrated Photonics Research 1999, OSA Technical Digest, Santa Barbara, California, Jul. 1999.

* cited by examiner

Primary Examiner—Frank G. Font
Assistant Examiner—Andrew H. Lee
(74) Attorney, Agent, or Firm—McDermott, Will & Emery

(57) ABSTRACT

A miniaturized chemical sensor features an optical microcavity coated with a surface layer, and a waveguide that evanescently couples light into the microcavity. The surface layer is adapted to chemically interact with one or more molecule species in a chemical vapor surrounding the microcavity, so as to alter the evanescent light coupling between the optical microcavity and the waveguide. The chemical interaction causes a change in the index of refraction of the microcavity, resulting in a measurable phase difference readout. The refractive index sensitivity is substantially increased, because of the high Q-value of the optical microcavity.

24 Claims, 7 Drawing Sheets

COATED OPTICAL MICROCAVITY RESONATOR CHEMICAL SENSOR

This application claims the benefit of provisional application No. 60/214,383 filed Jun. 28,2000.

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to optical sensors, and in particular to a high-resolution chemical sensor using a waveguide-coupled microcavity optical resonator.

BACKGROUND OF THE INVENTION

During the past few years, a substantial amount of research has been performed in the field of optical microcavity physics, in order to develop high cavity-Q optical microcavity resonators. In general, resonant cavities that can store and recirculate electromagnetic energy at optical frequencies have many useful applications, including high-precision spectroscopy, signal processing, sensing, and filtering. Many difficulties present themselves when conventional planar technology, i.e. etching, is used in order to fabricate high quality optical resonators, because the surfaces must show deviations of less than about a few nanometers. Optical microcavity resonators, on the other hand, can have quality factors that are several orders of magnitude better than typical surface etched resonators, because these microcavities can be shaped by natural surface tension forces during a liquid state fabrication. The result is a clean, smooth silica surface with low optical loss and negligible scattering. These microcavities are inexpensive, simple to fabricate, and are compatible with integrated optics.

Optical microcavity resonators have quality factors (Qs) that are higher by several orders of magnitude, as compared to other electromagnetic devices. Measured Qs as large at $10^{10}$ have been reported, whereas commercially available devices typically have Qs ranging from about $10^5$ to about $10^7$. The high-Q resonances encountered in these microcavities are due to optical whispering-gallery-modes (WGM) that are supported within the microcavities.

As a result of their small size and high cavity Q, interest has recently grown in potential applications of microcavities to fields such as electro-optics, microlaser development, measurement science, and spectroscopy. By making use of these high Q values, microspheric cavities have the potential to provide unprecedented performance in numerous applications. For example, these microspheric cavities may be useful in applications that call for ultra-narrow linewidths, long energy decay times, large energy densities, and fine sensing of environmental changes, to cite just a few examples.

In particular, a significant potential application for microcavity resonator devices is chemical/biological agent sensing. Chemical sensors known in the art include MEMS (microelectromechanical systems) chemical sensors, optical waveguide-based sensors, surface plasmon resonance (SPR) chemical sensors, surface acoustic wave (SAW) chemical sensors, mass spectrometers, and IR (infrared) absorption spectrometers. The sensitivities of many types of chemical sensors are limited by the small interaction region. On the other hand, spectrometers characterized by a high sensitivity, such as spectrometers using mass or optical detection properties, are large devices, and do not provide the advantages of miniaturized sensors, such as prior art MEMS sensors. The compact size of miniaturized sensors provide significant advantages. For example, miniaturized sensors are well adapted for in situ functioning. Also, miniaturized sensors would be small enough to be deployed in large numbers and implemented for remote probing.

It is therefore desirable to provide chemical sensors with an improved detection sensibility and resolution, while maintaining the compact size of miniaturized sensors, such as the MEMS sensors known in the art.

SUMMARY OF THE INVENTION

The present invention is directed to a miniaturized chemical sensor featuring an optical microcavity coated with a surface layer, and a waveguide that evanescently couples light into the microcavity. The surface layer interacts with at least one molecule species. The interaction alters the evanescent light coupling properties, typically through a change in refractive index of the microcavity. The waveguide is preferably a SPARROW (Stripline Pedestal Anti-Resonant Reflective Optical Waveguide) waveguide chip.

A chemical sensor constructed in accordance with the present invention includes a substrate, an optical waveguide disposed on the substrate, and an optical microcavity. The optical waveguide evanescently couples light into the microcavity. In one embodiment, the optical waveguide is an interferometric waveguide, including three waveguide arms: 1) an input channel for input coupling light into the microcavity; 2) a drop channel for out-coupling light from the microsphere into the waveguide; and 3) a reference channel that does not interact with the microcavity.

The optical microcavity is coated with a surface layer adapted to chemically interact with at least one molecule species. In one embodiment, the molecule species may be a molecule in a fluid or a gas. For example, the molecule species may be a molecule found in a chemical vapor surrounding the microcavity, by way of example. Alternatively, the molecule species may be a molecule found in a liquid solution. The chemical interaction causes a change in the index of refraction of the microcavity, and thus in the resonant frequency of the microcavity. By measuring the resonant frequency shift, or by measuring the phase difference readout caused by the change in the index of refraction, the molecule species may be detected.

A miniaturized chemical sensor constructed in accordance with the present invention provides a significantly increased sensitivity, as compared to prior art sensors. In one embodiment of the invention, a refractive index sensitivity of about $10^{-11}$ is achieved, representing an improvement of over three orders of magnitude, as compared to prior art waveguide chemical sensors.

DETAILED DESCRIPTION

The present invention features a miniaturized, increased sensitivity chemical sensor based on a waveguide-coupled microcavity resonator system. The chemical sensor includes an optical microcavity that is chemically coated with a surface layer, and an optical waveguide for evanescently coupling light onto the microcavity. The chemical interaction between the surface layer and one or more molecules in the chemical substance surrounding the microcavity, results in a measurable change in the evanescent coupling properties of the microcavity-waveguide system. In one embodiment, the measurable change is a change in the refractive index, which is detected as a change in the resonance frequencies of the WGMs, or a change in the phase difference that can be measured using an interferometric configuration.

Figure 1A:
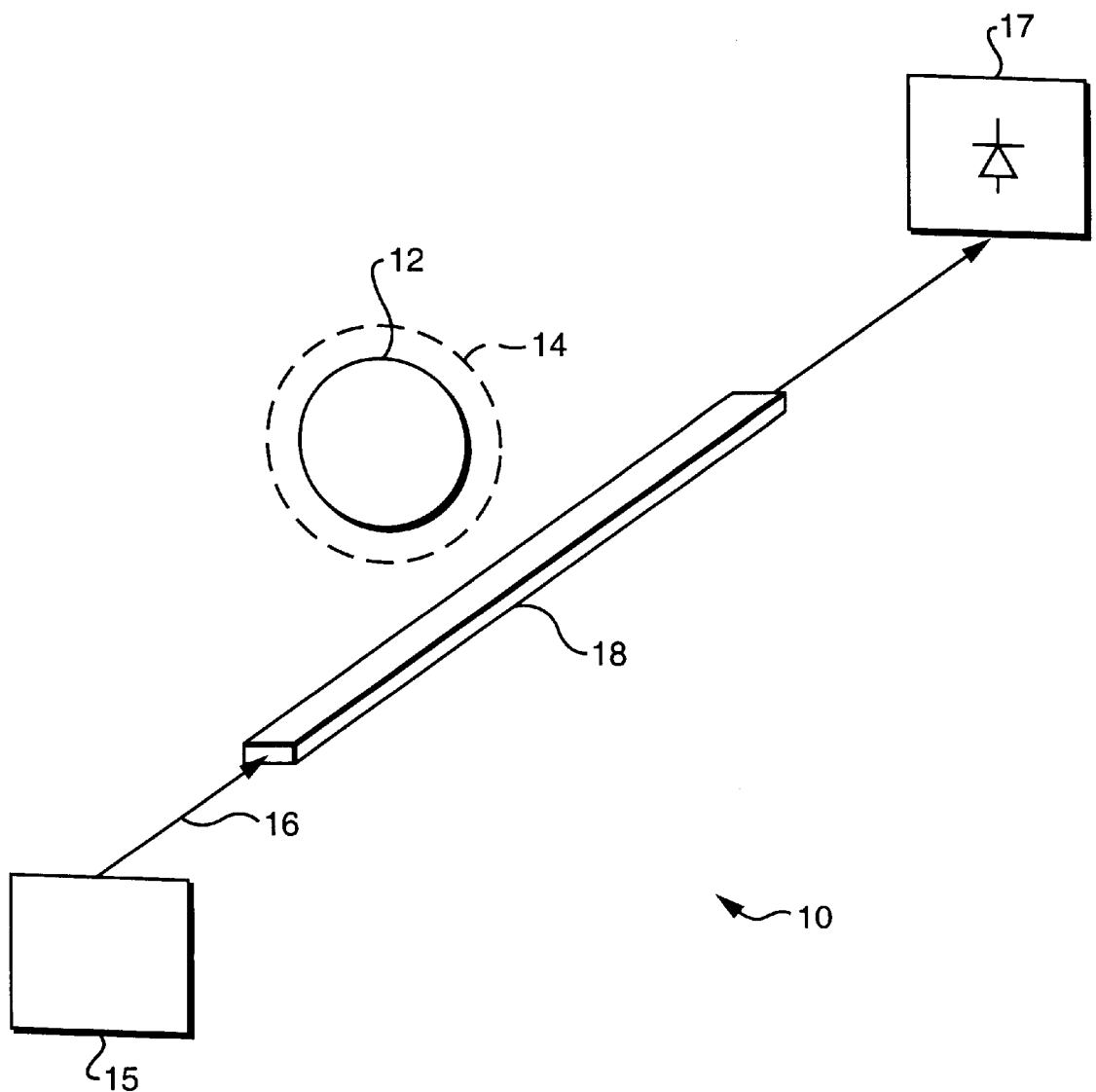
FIG. 1A is a schematic overview of a chemical sensor, constructed in accordance with the present invention.

FIG. 1A is an overview of one embodiment of a chemical sensor 10, constructed in accordance with the present invention. The chemical sensor 10 includes at least one optical microcavity resonator 12, and a waveguide 18 for evanescently coupling light from the waveguide 18 onto the microcavity 12. The microcavity 12 is chemically coated with a surface layer 14. Typically, the surface layer 14 has a thickness between a fraction of a monolayer and 1 micron. An optical source 15, preferably a laser, provides a beam 16 of input radiation directed to the waveguide. A photodetector 17 detects optical radiation transmitted through the waveguide 18.

The optical microcavity 12 is a small spherical particle, disk, or ring, having dimensions of the order of microns to millimeters. The optical microcavity 12 is typically made of silica. In a preferred embodiment, the optical microcavity 12 is fabricated by surface tension shaping of the tip of freshly melted optical fiber. Melting of the tip of a silica wire or fiber may be accomplished through arcing in a fusion splicer, by means of a gas flame, or using a high-power laser (such as a $CO_2$ laser) to heat the glass. Microcavities, with diameters typically ranging from about 50 micrometers to about 500 micrometers, are obtained by this method. In the illustrated embodiment, the optical microcavity has a diameter of about 200 micrometers, although other sizes are also within the scope of the present invention.

The optical microcavity 12 is adapted to support WGMs (whispering-gallery-modes), and is thus characterized by extremely high Q values. Light incident on an input end of the waveguide and propagating therethrough is evanescently coupled onto WGM resonances supported within the optical microcavity. An evanescent wave appears whenever a light wave undergoes total internal reflection at a dielectric interface, such as the interface between the silica waveguide and the surrounding air. The evanescent portion of the waveguide mode field is the exponentially decaying portion of the waveguide mode field, outside the relatively high index region of the waveguide. The evanescent wave decays exponentially with the distance from the surface of the waveguide core on a length scale of the order of the optical wavelength.

Evanescent coupling occurs between the waveguide and the microcavity when the wavelength of the evanescent field of the waveguide mode field matches the wavelength of a resonant WGM supported within the microcavity. In a resonant WGM, light is trapped near the surface of the microcavity by repeated total internal reflections, and travels in a circle around the microcavity near the surface of the microcavity. When WGM resonances are excited in the microcavity, light continues to circulate just inside the surface of the microcavity, with virtually no loss except for residual absorption and scattering in the dielectric. This is why extremely high Q-factors, up to over $10^{10}$, can be achieved in the dielectric microcavities constructed in accordance with the present invention. The cavity Q-factor of the microcavity can be determined by the linewidth of the resonance mode: the narrower the linewidth, the higher the cavity Q.

Figure 1B:
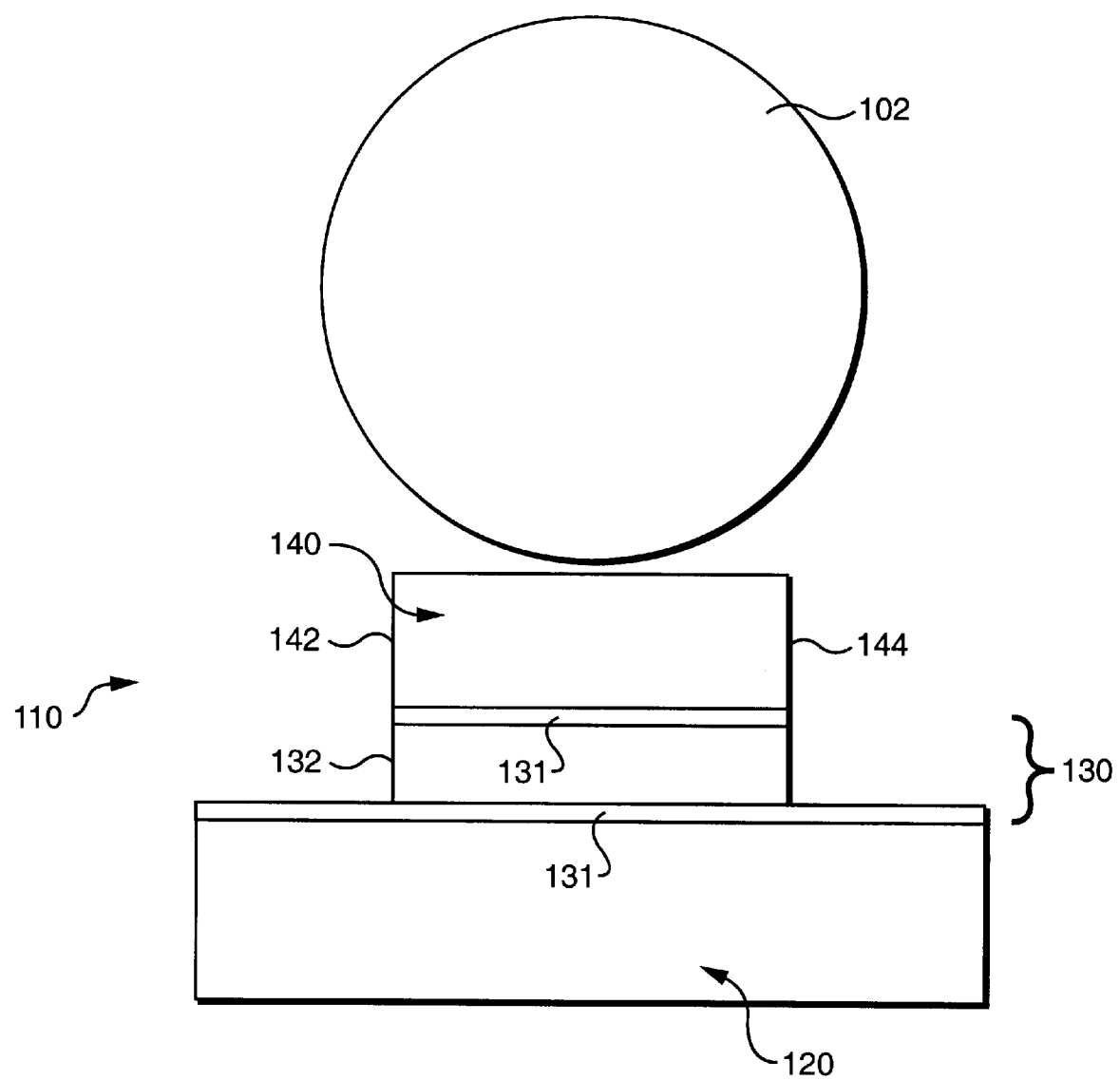
FIG. 1B illustrates a SPARROW optical waveguide, constructed in accordance with the present invention.

In a preferred embodiment, the optical waveguide is a SPARROW (stripline pedestal anti-resonant reflective optical waveguide) waveguide. FIG. 1B illustrates a SPARROW optical waveguide, constructed in accordance with the present invention. The SPARROW waveguide 110 provides an efficient and robust coupling mechanism for exciting whispering-gallery-modes in an optical microcavity 102. The SPARROW 110 includes a multi-layer, high-reflectivity dielectric stack 130 disposed on the substrate 120, and a waveguide core 140. The substrate 120 is substantially planar, and in one embodiment is made of silicon.

The dielectric stack 130 is composed of alternating high ($n_H$) and low ($n_L$) refractive index layers 131 and 132, made of a dielectric material. As a result, the dielectric stack 130 functions as a high reflectivity dielectric mirror. The larger the number of layers 131 and 132, the higher the reflectivity of the stack 130 becomes. While the illustrated embodiment includes only one low index layer 132 disposed between two high index layers 131, the number of the layers 131 and 132 can be increased in order to increase the reflectivity of the stack 130. The alternating layers 131 and 132 forming the dielectric stack 130 provide a cladding for the SPARROW waveguide core 140, i.e. the layers forming the stack 130 may be regarded as cladding layers.

The high reflectivity of the dielectric stack 130 permits isolation of the optical modes of the microcavity 102 and the waveguide core 140 from the waveguide cladding and the substrate. By isolating the waveguide core 140 using the high-reflectivity dielectric stack 130, the SPARROW 110 circumvents the need for obtaining low refractive index cladding materials. As shown in FIG. 1A, one of the high refractive index layers 131 is in contact with the substrate 120.

In one embodiment, the high refractive index layer 131 is made of Si (silicon), while the low refractive index layer 132 is made of $SiO_2$ (silica). In one embodiment, the high refractive index nH is about 3.5, and the low refractive index $n_L$ is about 1.45, although other refractive indices are also within the scope of the present invention. The refractive indices required for efficiently guiding light within the waveguide depend on the wavelength of optical radiation.

The waveguide core 140 is disposed on top of the dielectric stack 130, and is in contact with another one of the high refractive index layers 131. The waveguide core 140 includes an input end 142 and an output end 144, and is adapted for transmitting optical radiation incident on the input end 142 to the output end 144. In one embodiment, the waveguide core is made of silica, and is characterized by the low refractive index nL. In a SPARROW waveguide, the waveguide mode field is essentially entirely contained within the waveguide core 140 on top of the dielectric stack 130, and is isolated from the substrate 120. The successful elimination of both the microcavity mode and the waveguide mode leakage into the substrate results in extremely high coupling efficiencies. Coupling efficiencies approaching 100% have been observed.

Figure 2:
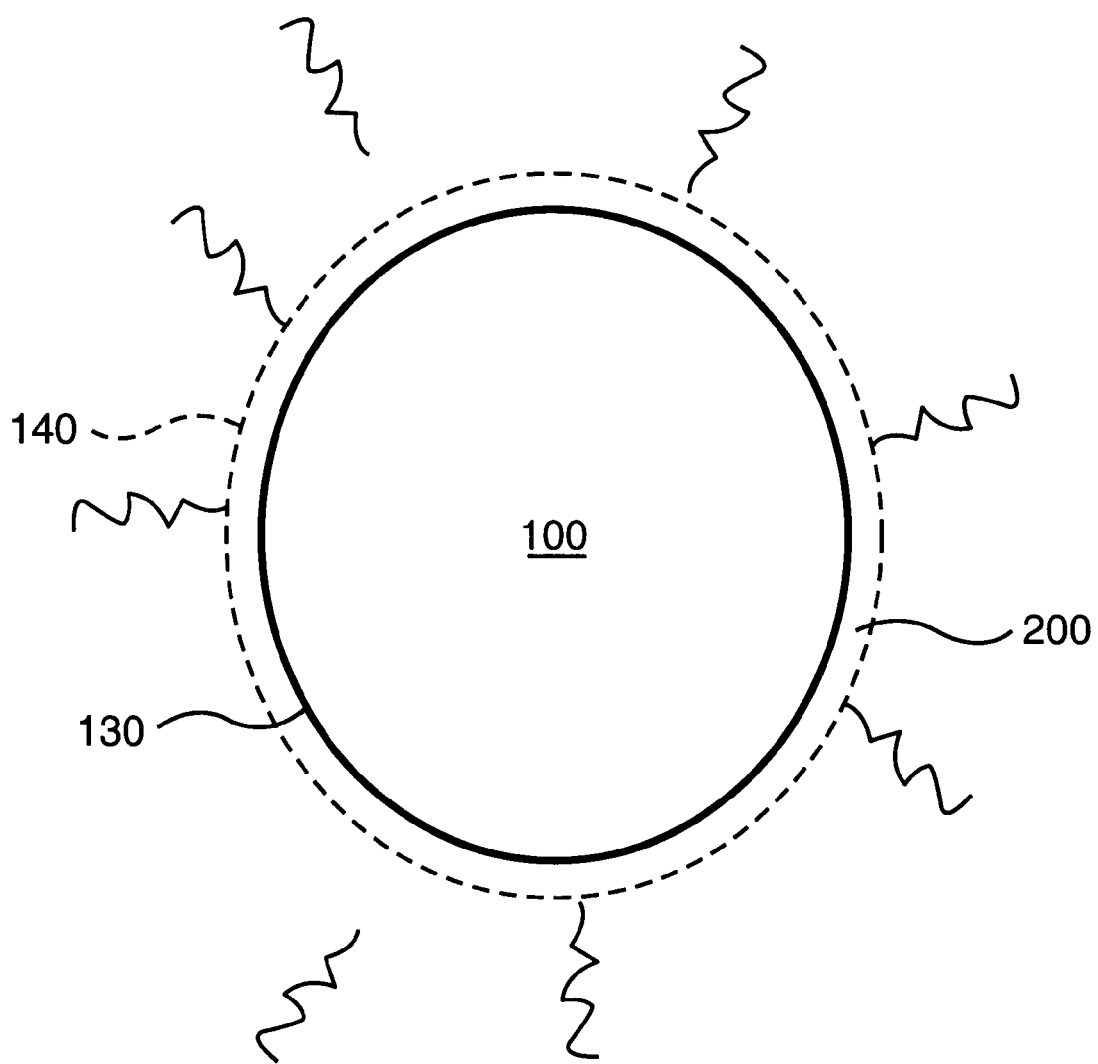
FIG. 2 illustrates an optical microcavity constructed in accordance with the present invention and including a surface layer adapted to interact with a molecule species.

FIG. 2 illustrates a chemically coated optical microcavity 100, constructed in accordance with the present invention. The optical microcavity 100 includes a surface layer 200, which is formed by applying a thin film of chemical coating to the surface of the microcavity 100. The thin film is formed of one or more molecular layers, with film thickness ranging from a fraction of a monolayer to 1 micron, depending on the desired sensor response time and sensitivity. The surface layer 200 is adapted to chemically interact with at least one molecule species, so as to alter the optical interaction between the optical microcavity and waveguide core by changing the index of refraction of the optical microcavity. In one embodiment of the invention, the molecule species is part of a chemical vapor surrounding the microcavity 100. Alternatively, the molecule species may be a molecule within an acqueous liquid, or within other types of fluids.

In the illustrated embodiment of the invention, the coating deposited on the microsphere consists of a plurality of thin films, although in other embodiments a single thin film can be used. The coating includes a bottom layer 130, and a top layer 140. In this embodiment, the bottom layer 130 serves to protect the surface of the microcavity in order to prevent undesired surface interactions, such as interactions with atmospheric water. The top layer 140 is chosen to perform a selected chemical reaction that changes in the optical coupling between the microcavity and the waveguide, for example by changing the index of refraction of the microcavity 100.

The microcavity 100 is adapted to chemically interact, through its surface layer, with one or more molecules in a chemical substance. The chemical reaction changes the index of refraction of the microcavity 100. The change in the index of refraction alters the phase difference acquired by the resonant light circulating within the microcavity 100, as compared to throughput light that has been transmitted through the waveguide without being coupled into the microcavity 100. Along with a change in the phase difference, the change in refractive index of the microcavity alters the resonant frequencies of the microcavity WGMs. These readout techniques, phase difference and WGM frequency, allow the molecule species to be detected with significantly increased precision.

In one embodiment of the invention, the chemical interaction between the top layer 140 and the molecules in a chemical substance is an adsorption reaction. In an adsorption process, at least one molecule forming the chemical vapor is adsorbed into the surface layer. As a result, the index of refraction of the surface layer 140 changes. In another embodiment, the chemical interaction may be a polymerization process. In this embodiment, the top layer 140 is a molecular film, selected so that when a molecule of interest adsorbs onto the surface, a polymerization reaction occurs, thus changing the resonance mode coupling. In another embodiment, the chemical interaction of the top layer 140 with one or more molecules forming the chemical vapor surrounding the microcavity 100 is a bonding of the molecule with the surface layer. The bonding causes a change in the refractive index of the optical microcavity.

The change in refractive index results in a measurable phase difference readout from the interferometric waveguide 18. In one embodiment, the optical waveguide 18 may have a Mach-Zehnder interferometric configuration, adapted to measure the phase difference readout resulting from the change in refractive index of the optical microcavity. In this embodiment, the waveguide 18 includes a splitter for splitting said input optical radiation into a first signal and a second signal, a first and a second waveguide branch for transmitting the first and second signals, and a combiner for recombining the first and second signals.

As known in the art, an incoming optical signal in a Mach-Zehnder interferometer is split into two signals, $E_1$ and $E_2$, for example at a Y-junction. Each signal enters a first and a second waveguide branch, respectively. The signals are recombined into an output waveguide, which provides a modulated optical output signal, $E_3$ ($E_3 = E_1 + E_2$). The Mach-Zehnder modulator is typically formed of materials that have a high. electro-optic coefficient, so that their refractive indices can be altered by applying an electric field in that region. An electric field applied to one or both of the waveguide branches causes a change in the refractive index in the applied region, corresponding to the changing amplitude of the modulating signal. The change in the index of refraction results in a change in the delay time of the light passing through the region. The optical path length in one or both of the waveguides branches can be controlled, so that a phase difference results between the two signals $E_1$ and $E_2$, when they are recombined at the output waveguide.

Figure 3:
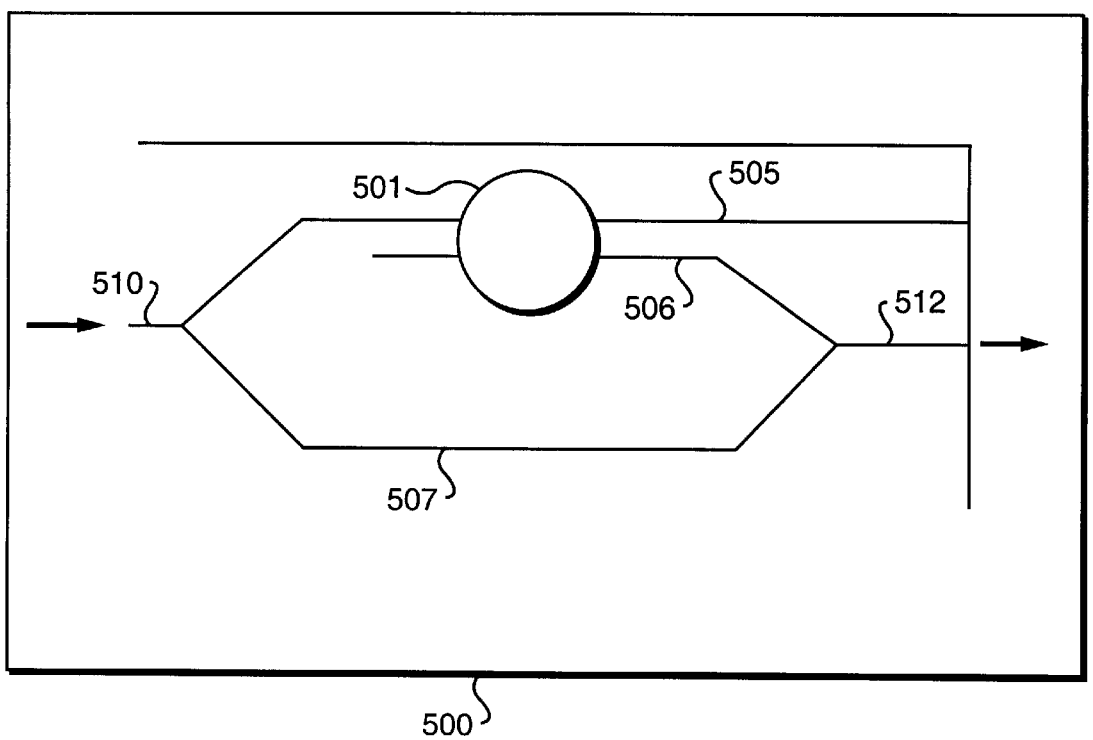
FIG. 3 illustrates an optical waveguide constructed in accordance with the present invention and having a Mach-Zehnder type interferometric configuration.

FIG. 3 illustrates a three-armed waveguide 500 having a Mach-Zehnder type interferometric configuration. The waveguide 500 has an input end 510 and an output end 512. The interferometric waveguide 500 includes three waveguide arms 505, 506, and 507. The first arm 505 forms an input channel, and is adapted to input coupling light into the microsphere. The second arm 506 forms a drop channel, and is adapted to out-couple light from the microcavity into the waveguide. The third arm 507 is used as a reference channel, which has substantially no interaction with the microcavity. At the output end 512, light from the reference channel 507 is combined or interfered with light from the drop channel, i.e. light that has interacted with the microsphere.

The change in refractive index of the optical microcavity causes a measurable change in phase experienced by the resonant light circulating within the microcavity, since the cavity lifetime r(d) for resonant light within the microcavity is related to the total cavity Q:

$$\tau(d) = \frac{Q(d)}{\omega}$$

where d is the coupling gap between the microcavity and the waveguide. Assuming interferometer arms of equal path length, the OPD l(d) can then be expressed as a function of the cavity lifetime, $$l(d) = \frac{c}{n}\tau(d) = \frac{\lambda}{2\pi n}Q(d)$$

The change in the refractive index of the microcavity alters the resonant frequencies of the microcavity WGMs.

Figure 4A:
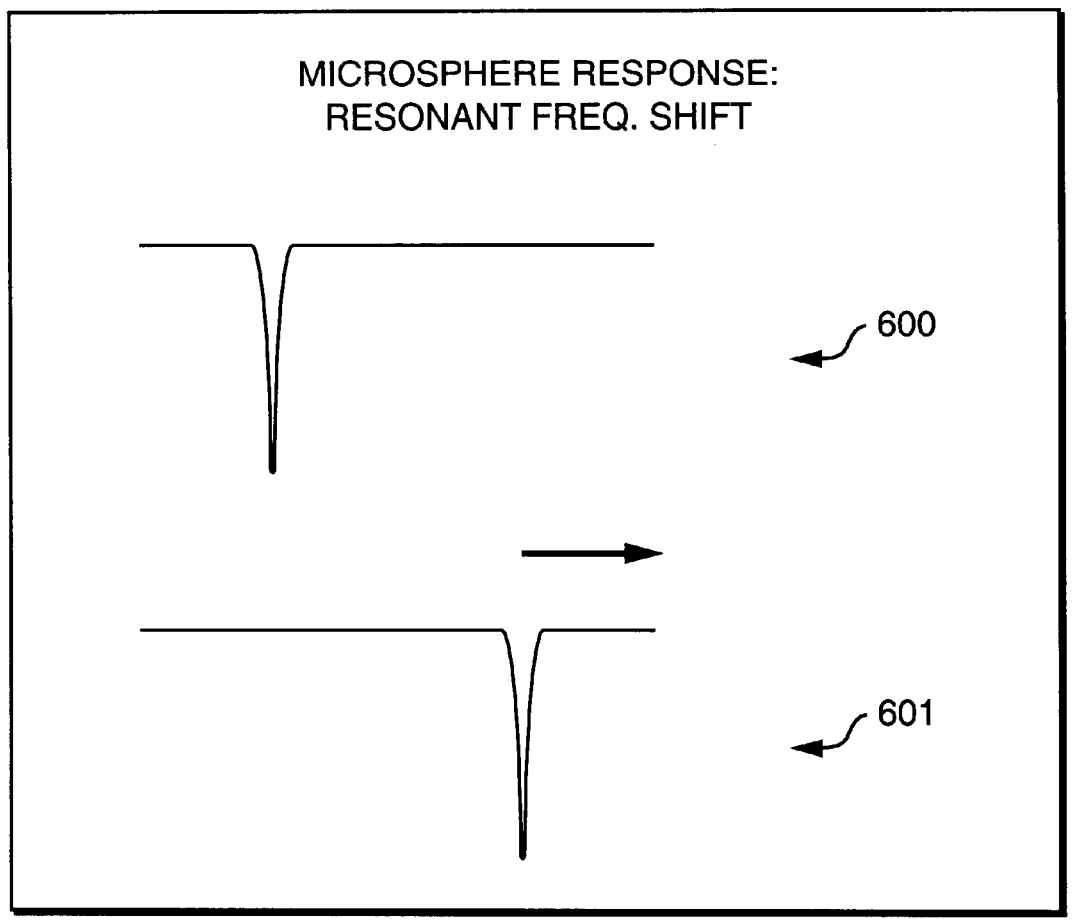
FIG. 4A schematically illustrates a resonant frequency shift caused by the interaction of a surface layer of a microcavity with one or more molecules.

FIG. 4A graphically illustrates a resonant frequency shift caused by the interaction of a surface layer of a microcavity with one or more molecules. The graph labeled as 600 illustrates the resonant frequency of the microcavity in the absence of a chemical substance that interacts with the surface layer, while the graph labeled as 601 illustrates the resonant frequency of the microcavity in the presence of a chemical substance that interacts with the surface layer.

Figure 4B:
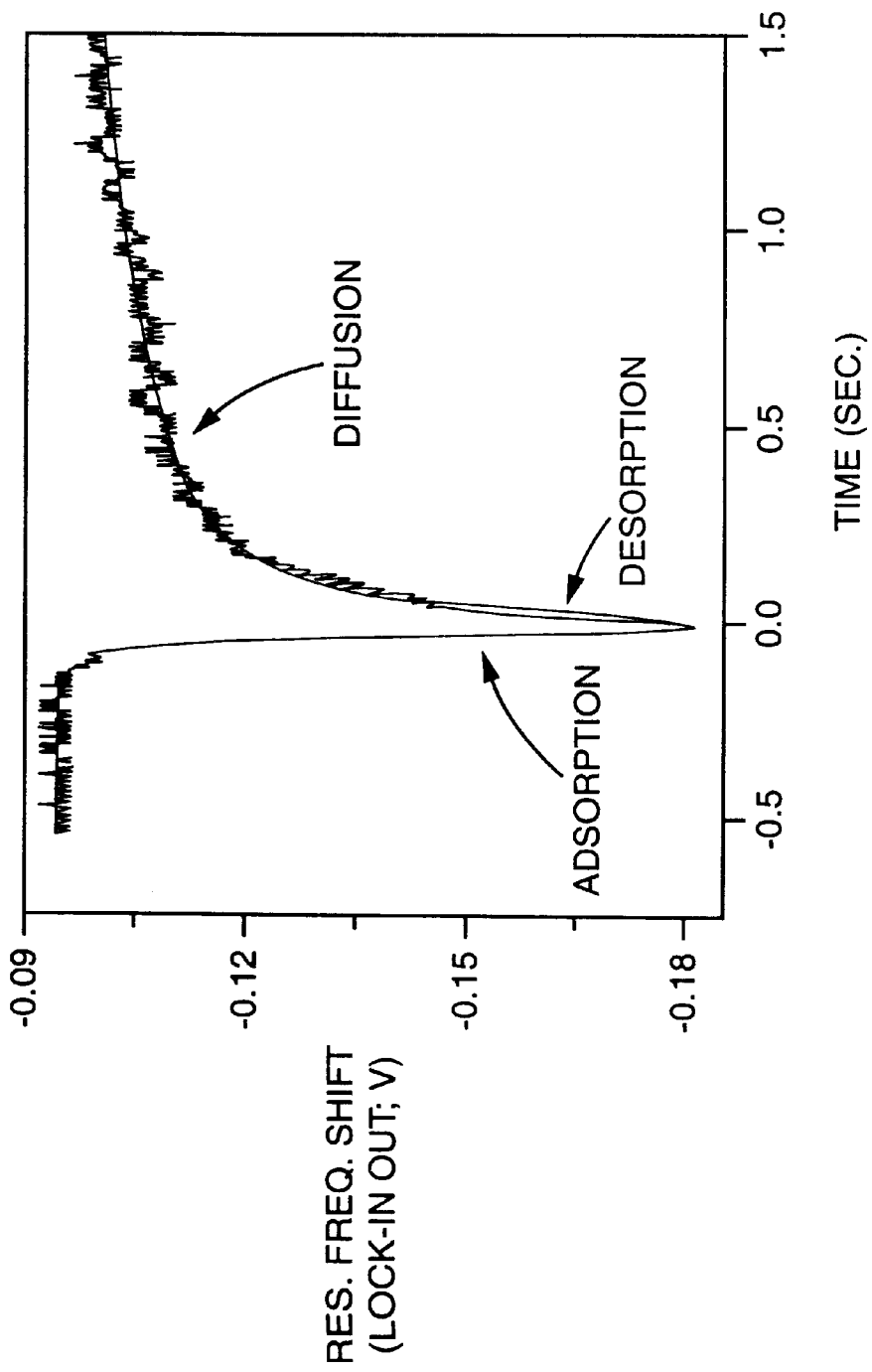
FIG. 4B illustrates a resonant frequency shift resulting from a silica microsphere interaction with acetic acid.

FIG. 4B illustrates a resonant frequency shift resulting from a silica microsphere interaction with acetic acid. The measured refractive index resolution, as determined from the graph, is about 3 times $10^{-8}$. Other molecular vapors that induce a microsphere response include, but are not limited to, dimethy methyl phosphonate (DMMP), triethyl amine (TEA), acetic acid, and isopropyl alcohol.

Figure 5:
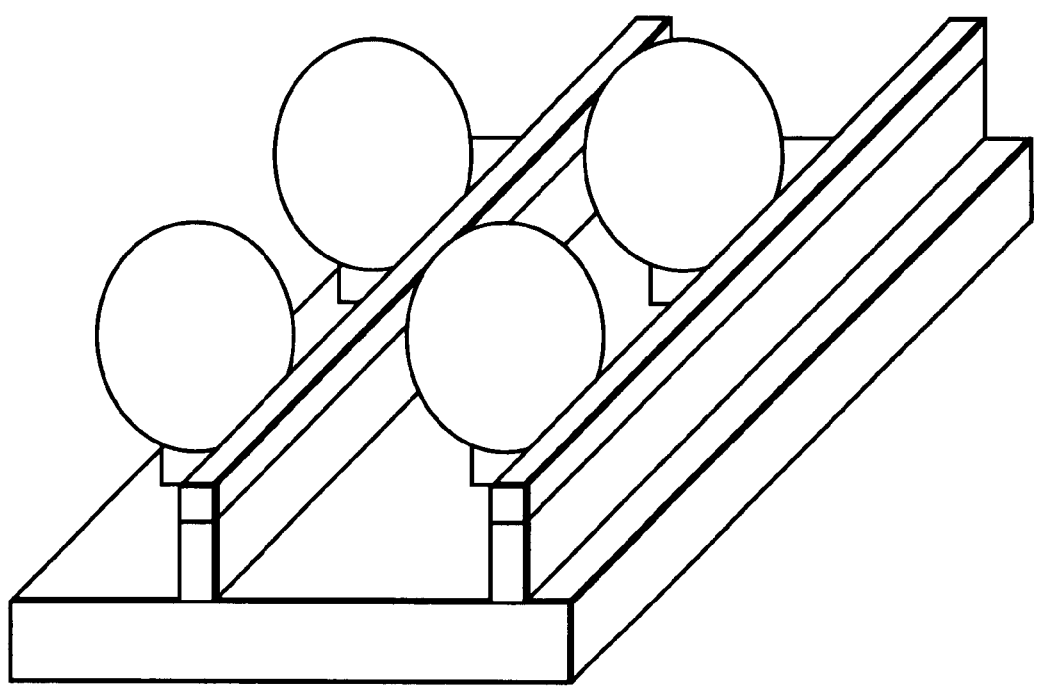
FIG. 5 illustrates a schematic diagram of a microcavity array integrated optical chip, including a plurality of microcavities.

In one embodiment of the invention, a micro-optic distributed chemical sensor that consists of multiple spheres of different sizes may be constructed. FIG. 5 illustrates a schematic diagram of a microcavity array integrated optical chip, including a plurality of microcavities. A plurality of microcavities, each coated with a different surface layer, is integrated into a single, compact sensing unit. Each microcavity includes a surface layer which is selective for a specific chemical. Since the spheres are all characterized by different sizes, their resonance frequencies are all different and can therefore be probed individually.

Because of the use of microcavity resonators, the chemical sensor disclosed in the present invention provides a significantly increased refractive index sensitivity, as compared to prior art chemical sensors, such as conventional optical waveguide chemical sensors. A chemical sensor constructed in accordance with the present invention provides the advantages of a compact size, comparable to MEMS sensors, together with high sensitivity. The present invention may have wide ranging applications in the industry and the military, including but not limited to the fields of manufacturing process control, environmental monitoring, and chemical agent sensing on the battlefield.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An optical resonator sensor, comprising:
    A. a substrate;
    B. an optical waveguide having an input end and an output end, said waveguide for transmitting optical radiation incident on said input end to said output end;
    C. at least one optical microcavity constructed and arranged so as to optically interact with optical radiation propagating through said optical waveguide;
wherein said optical microcavity includes at least one surface layer to interact with at least one molecule species so as to alter the optical interaction between said optical microcavity and said waveguide.

2. An optical resonator sensor according to claim 1, wherein said optical microcavity is disposed at a distance from said optical waveguide that is sufficiently small so as to allow evanescent coupling between said microcavity and said optical waveguide.

3. An optical resonator sensor according to claim 1, wherein said optical waveguide comprises:
    a splitter for splitting said input optical radiation into a first signal and a second signal;
    a first waveguide branch and a second waveguide branch for transmitting said first signal and said second signal, respectively; and
    a combiner for recombining said first signal and said second signal.

4. An optical resonator sensor according to claim 1, wherein said optical waveguide includes channels arranged in a Mach-Zehnder interferometer configuration.

5. An optical resonator sensor according to claim 1, wherein said optical waveguide core includes a drop channel, a throughput channel, and a reference channel, arranged so that the optical microcavity can optically interact with both the drop channel and the throughput channel, but does not substantially optically interact with light in the reference channel.

6. An optical resonator sensor according to claim 1, wherein the surface layer interaction with said molecule species comprises a chemical reaction between said molecule species and said surface layer that alters the optical interaction between said optical microcavity and said optical waveguide.

7. An optical resonator sensor according to claim 1, wherein said alteration in optical coupling is caused by a change in the index of refraction of said optical microcavity.

8. An optical resonator sensor according to claim 1, wherein the chemical reaction comprises polymerization of said surface layer.

9. An optical resonator sensor according to claim 1,
    wherein the surface layer interaction with said molecule species comprises a bonding of said molecule species with said surface layer, and
    wherein said bonding causes a change in refractive index of said optical microcavity.

10. An optical resonator sensor according to claim 1, wherein the surface layer interaction with said molecule species comprises adsorption of said molecule species by said surface layer, whereby said adsorption causes a shift in the resonant frequency of at least one cavity mode of said optical microcavity.

11. An optical resonator sensor according to claim 2, wherein said evanescent field is characterized by a frequency substantially equal to a resonant mode of said optical microcavity.

12. An optical resonator sensor according to claim 2, wherein said resonant mode of said optical microcavity is a whispering gallery mode.

13. An optical resonator sensor according to claim 2,
    wherein said optical microcavity is characterized by a radius r; and
    wherein the wavelengths of the whispering gallery modes of said microcavity are substantially equal to the values of λ given according to the formula:

$$2\pi r = n\lambda,$$

n being a nonzero integer.

14. An optical resonator sensor according to claim 1, wherein said surface layer of said optical microcavity includes a gold layer.

15. An optical resonator sensor according to claim 1, wherein said optical microcavity is selected from the group consisting of microspheres, microdisks, and microrings.

16. An optical resonator sensor according to claim 1, further comprising a light source arranged to input light into said input end of said optical waveguide.

17. An optical resonator sensor according to claim 1, further comprising at least one detector constructed and arranged so as to detect output optical radiation from said output end of said optical waveguide.

18. An optical resonator sensor according to claim 1, wherein said optical microcavity is made of silica.

19. An optical resonator sensor according to claim 1, wherein said optical waveguide is an integrated optical chip.

20. An optical resonator sensor according to claim 1, wherein said optical waveguide comprises:
(a) a multi-layer dielectric stack disposed on said substrate, said dielectric stack including alternating high and low refractive index dielectric layers; and
(b) a waveguide core disposed on said dielectric stack and having an input end and an output end, said waveguide core being adapted for transmitting optical radiation incident on said input end to said output end.

21. An optical resonator sensor according to claim 20, wherein one of said low refractive index layers is in contact with said substrate, and wherein one of said high refractive index layers is in contact with said waveguide core.

22. An optical resonator sensor according to claim 20, wherein said low index dielectric layer and said waveguide core comprises silica.

23. An optical resonator sensor according to claim 20, wherein said high index dielectric layer comprises silicon.

24. An optical resonator sensor according to claim 1, wherein said surface layer interaction with said at least one molecule species alters the resonant frequency of at least one cavity mode of at least one of the at least one optical microcavity.

* * * * *